United States Patent
Rasche et al.

(10) Patent No.: US 8,160,337 B2
(45) Date of Patent: Apr. 17, 2012

(54) IMAGING SYSTEM FOR THE GENERATION OF HIGH-QUALITY X-RAY PROJECTIONS

(75) Inventors: Volker Rasche, Erbach (DE); Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 819 days.

(21) Appl. No.: 11/576,702

(22) PCT Filed: Oct. 6, 2005

(86) PCT No.: PCT/IB2005/053292
§ 371 (c)(1),
(2), (4) Date: Nov. 19, 2008

(87) PCT Pub. No.: WO2006/040715
PCT Pub. Date: Apr. 20, 2006

(65) Prior Publication Data
US 2009/0080751 A1 Mar. 26, 2009

(30) Foreign Application Priority Data
Oct. 11, 2004 (EP) .................................... 04300671

(51) Int. Cl.
*G06K 9/00* (2006.01)
(52) U.S. Cl. ...................................................... 382/131
(58) Field of Classification Search .......... 382/128–132; 378/62
See application file for complete search history.

(56) References Cited

U.S. PATENT DOCUMENTS

| 4,672,649 | A | 6/1987 | Rutt |
| 5,371,778 | A | 12/1994 | Yanof et al. |
| 5,722,408 | A | 3/1998 | Dehner et al. |
| 5,841,830 | A * | 11/1998 | Barni et al. ..................... 378/15 |
| 6,222,902 | B1 | 4/2001 | Lin et al. |
| 6,243,436 | B1 | 6/2001 | Hahn et al. |
| 2004/0062343 | A1 | 4/2004 | Brunnett et al. |

FOREIGN PATENT DOCUMENTS

| EP | 0365141 A | 4/1990 |
| EP | 0860144 A | 8/1998 |

OTHER PUBLICATIONS

S. Eiho; "A Display System for Objects With Three Dimensional Tomographic Data", Third Intl Conf. on Image Proc. and its Appl. (Conf. Publ. No. 307), IEE London, UK, 1989, pp. 373-377, XP006517425.

Y. Saito et al; "Development and Evaluation of a Real-Time Three-Dimensional CT (4D-CT) Scanner", Proc. of the SPIE—The Intl Society for Optical Eng. SPIE-Int. Soc. Opt. Eng USA, vol. 4682, 2002, pp. 801-808, XP002358003.

* cited by examiner

*Primary Examiner* — Courtney Thomas

(57) ABSTRACT

The invention relates to an imaging system and a method for generating high-quality X-ray projections (24) of a patient (1). The system comprises a rotational X-ray device (10), for example a cone-beam CT-gantry (12), and an associated data processing unit (20). During a medical intervention, low-dose raw projections (22) of the patient (1) are continuously generated from different directions. A volume of interest (23) is then reconstructed from said projections (22), from which high-quality virtual projections (24) can be calculated for a display on a monitor (25). The number and direction of said virtual projections (24) can be arbitrarily chosen by the user.

10 Claims, 2 Drawing Sheets

IMAGING SYSTEM FOR THE GENERATION OF HIGH-QUALITY X-RAY PROJECTIONS

Figure 1:
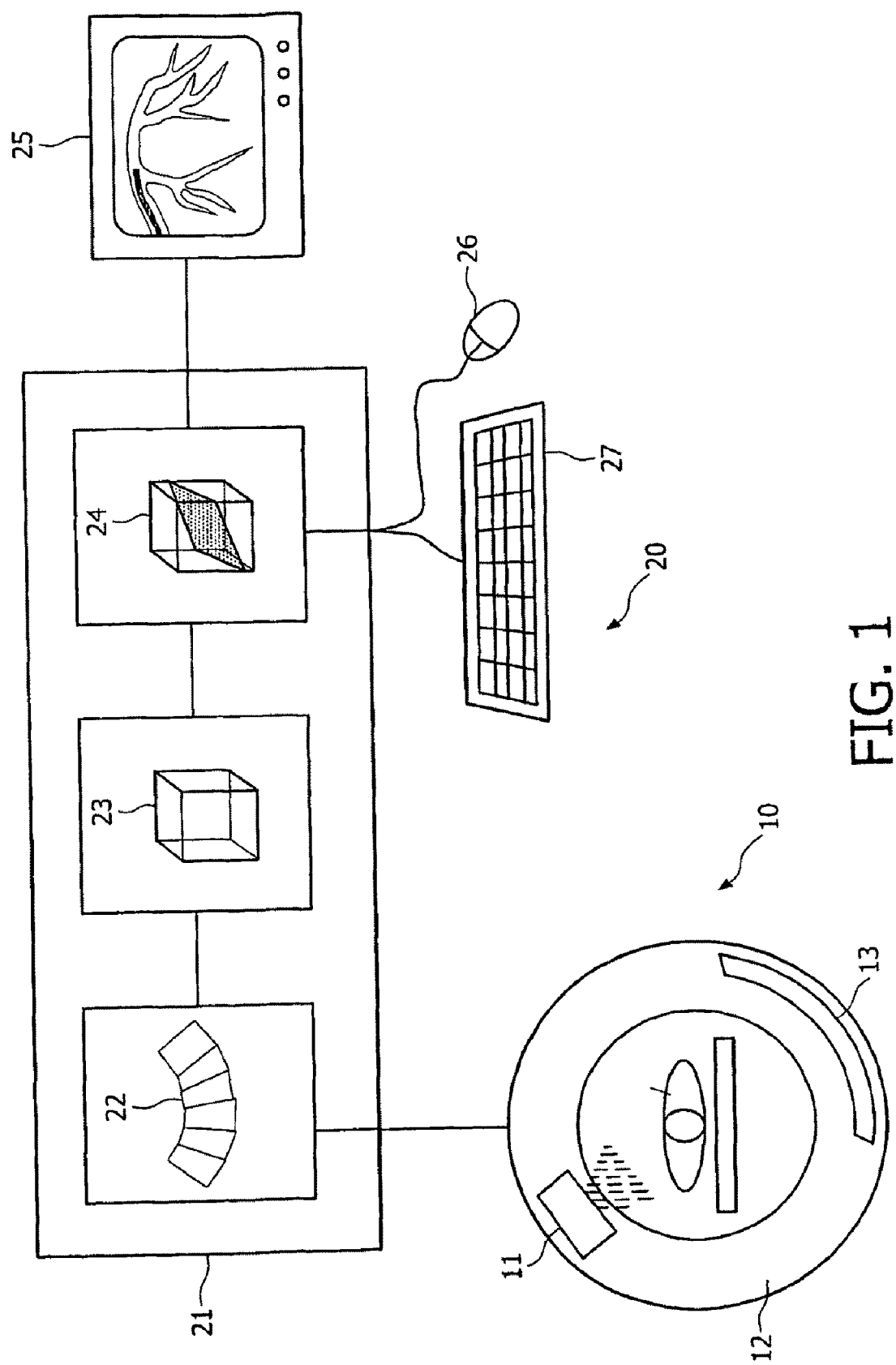

The invention relates to an imaging system, a method, and a record carrier for the generation of X-ray projections of an object in real time.

During medical interventions, e.g. an examination or treatment of the vascular system with a catheter, it is desirable to monitor the processes inside the body of a patient in real time. This is typically done by X-ray fluoroscopy, i.e. the continuous generation of two-dimensional X-ray projections of a region of interest. A drawback of this procedure is however that the direction of the projections can, if at all, only be changed slowly and within a limited angular range. Moreover, the quality of the projections may be low due to anatomical noise, i.e. structures like bones that lie in front and behind the field of view and are superimposed in the projection.

From the U.S. Pat. No. 6,222,902 B1 a special imaging system is known with an X-ray source that can rotate on a circle below a patient while the associated two-dimensional detector remains stationary. The projections that are generated by said device are used for the reconstruction of different parallel focal plains (slices) within the patient according to the principle of tomosynthesis. Moreover, it is possible to synthesize a series of slices to a three-dimensional representation of a volume.

Based on this situation it was an object of the present invention to provide means for the flexible generation of X-ray projections of a patient that may particularly be used for monitoring in medical interventions.

This object is achieved by an imaging system according to claim 1, by a method according to claim 9, and by a record carrier according to claim 10. Preferred embodiments are disclosed in the dependent claims.

According to its first aspect, the present invention relates to an imaging system for the generation of X-ray projections of an object in real time, wherein the quality of said projections should in one or more respect (e.g. signal-to-noise-ratio, contrast) be equal to or better than the quality of a conventional, directly taken X-ray projection with optimal parameter settings (dose, exposure time etc). Moreover, the term "real time" shall refer to conditions under which the projection image of a certain situation is available with a negligible latency of for example 0.1 to 3 s, preferably 0.1 to 0.5 s. Additionally, a temporal process should run in the corresponding "real time" series of projections as fast as in reality, i.e. without "slow motion" effects. The required availability of projections in real time makes them particularly suitable for a monitoring or guidance application in medical interventions. The imaging system comprises the following components:

a) A rotational X-ray device which by definition comprises an X-ray source that can be moved on a curved trajectory, for example a closed circle. Moreover, said device shall be adapted to generate X-ray raw projections of the object from different directions and particularly with a low dose setting.

b) A data processing unit that is adapted to reconstruct a volume of interest from a set of the aforementioned raw projections generated by the X-ray device, and to calculate at least one virtual projection of predetermined parameters (e.g. the projection direction) from the reconstructed volume of interest or a sub-volume (region of interest, ROI) of the reconstructed volume of interest. Said virtual projection then corresponds to the high-quality projection searched for. The reconstruction of the volume of interest can be achieved with standard algorithms known from Volume Computed Tomography (VCT), and the operation of the data processing unit can practically be made as fast as required by providing it with enough processing power.

An imaging system of the aforementioned kind has two main advantages over conventional X-ray devices that generate a sequence of projections from a stationary direction: First, the use of virtual projections that are calculated from a reconstructed volume allows choosing the projection direction arbitrarily. Thus it is for example possible to switch instantaneously between different directions, to look at several projections from different directions simultaneously (e.g. a stereo display), or to look from directions that cannot be assumed by the X-ray apparatus itself due to mechanical constraints. The second important advantage of the imaging system is that the quality of the virtual projections is higher than the quality of the direct raw projections from the same direction. This is due to the fact that the virtual projection integrates information of raw projections from different directions, which allows to achieve a better signal-to-noise-ratio and to reduce for example anatomical noise. It should be noted in this respect that the high quality of the virtual projections can be achieved without exposing the patient to excessive doses of X-radiation, because the single raw projections can be generated with low doses. In summary, the imaging system generates a plurality of low dose/low-quality projections, reconstructs a low quality volume from the projections, and then calculates single high-quality virtual projections from said volume.

According to a preferred embodiment of the invention, the rotational X-ray device comprises a cone-beam X-ray source and a two-dimensional X-ray detector. Said components may be rigidly fixed to each other on a (circular) C-arm and/or be disposed in a gantry that allows them to rotate around an object. The cone-beam and the two-dimensional detector array make it possible to project a volume of the object in one sweep, so that no helical movement of the device is necessary as in many conventional CT systems.

Often only a small region within an object is of interest at a time, for example the tip of a catheter or a lesion in the vessel system. In order to reduce computing load in such cases, the volume that is reconstructed by the data processing unit may optionally be limited to such a region which is smaller than the volume that might maximally be reconstructed from the set of raw projections.

As was already mentioned, the raw projections are preferably generated with a low dose setting, wherein the quantitative definition of a "low dose" depends on the individual situation, particularly the kind of object that is imaged. Preferably, the accumulated total dose over a set of projections which is used for the reconstruction of a volume of interest is approximately equal to the dose of a single projection generated with optimal quality (high contrast, good signal-to-noise-ratio etc.).

According to a preferred embodiment of the imaging system, the dose of the X-ray device can be interactively switched between different dose levels. This allows particularly to switch between a low-dose mode in which virtual projections are generated and a high-dose mode in which reconstructed volumes of high quality are considered.

In an optional embodiment, the rotational X-ray device is adapted to rotate over more than 360°, i.e. continuously in one direction on a closed trajectory, and with a speed of at least four Hz (revolutions per second).

Moreover, the rotational X-ray device is preferably adapted to generate X-ray raw projections at a rate of more than 100 projections (frames) per second, preferably more than 150 projections per second. These high rates together with the aforementioned rotational speed guaranty that enough projections from different directions are available for the reconstruction of volumes that represent processes in the body in real time.

In another a preferred embodiment of the invention, the data processing unit is adapted to update the reconstructed volume of interest continuously based on new raw projections. This means that the volume of interest is at any time reconstructed from the most recent raw projections that are available, thus guaranteeing that always the actual situation in the body is depicted. The reconstruction of the volume may be updated each time a certain number (e.g. from 1 to 30) of new raw projections is available or each time the X-ray device has moved forward a certain angle (e.g. 30°).

The imaging system may optionally comprise a display unit for the display of the reconstructed volume of interest, of raw projections and/or particularly of calculated virtual projections. Moreover, the display unit should be adapted to display stereo images of the aforementioned volume, raw projections or virtual projections, i.e. images with viewing angles that correspond to the viewing angles of the human eyes in such a way that they can be mentally composed to a three-dimensional image.

The imaging system may further comprise an input device for the interactive determination of parameters of the raw projections, the volume of interest and/or of the virtual projections, for example a keyboard, a mouse or a touch screen. Thus the user may for example adapt the viewing angle of the virtual projections, the location of the volume of interest, or the parameters for the generation of the raw projections.

The invention further comprises a method for the generation of X-ray projections of an object in real time, comprising the following steps:

a) generating (preferably low dose) X-ray raw projections of the object from different directions;
b) reconstructing a volume of interest from said raw projections;
c) calculating at least one virtual projection from the reconstructed volume of interest or a sub-volume thereof.

Finally, the invention comprises a record carrier, for example a floppy disk, a hard disk, or a compact disc (CD), on which a computer program for the generation of high-quality X-ray projections of an object in real time is stored, wherein said program is adapted to execute a method of the aforementioned kind.

The method and the record carrier have the same basic features as the imaging systems that were described above. For more information on details, advantages and further developments of them reference is therefore made to the description of the imaging system.

These and other aspects of the invention will be apparent from and elucidated with reference to the embodiment(s) described hereinafter.

Figure 2:
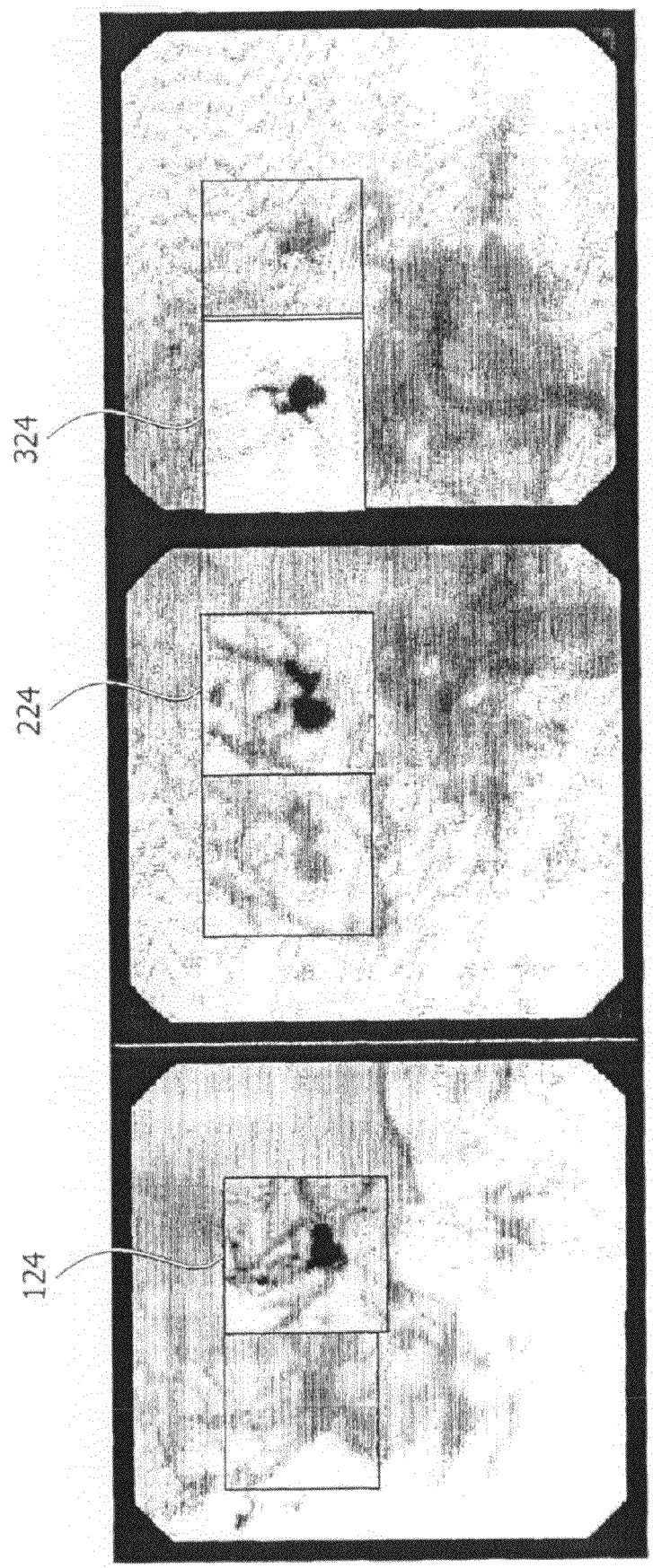

In the following the invention is described by way of example with the help of the accompanying drawings in which:

FIG. 1 schematically depicts an imaging system according to the present invention;

FIG. 2 shows a comparison between raw projections of an aneurysm and the corresponding virtual projections calculated according to the present invention.

A principal sketch of an imaging system according to the present invention is shown in FIG. 1. The system comprises a rotational X-ray device 10 that may for example be identical or similar to a CT system. The device 10 comprises an X-ray source 11 for the generation of a cone-beam of X-rays, and a two-dimensional X-ray detector 13 (e.g. a flat dynamic X-ray detector FDXD) that is located opposite to the X-ray source in order to measure radiation transmitted through the patient 1 lying in the centre of the device. The X-ray source 11 and the detector 13 are guided in a circular gantry 12 and can synchronously rotate around the patient 1 with a frequency of preferably about 5 Hz. Moreover, they are adapted to generate during rotation X-ray projections of the patient 1 with a rate of preferably more than 150 frames/s, wherein said projections are generated with a comparatively low dose. Thus the strain of the patient with radiation can be limited in spite of the continuous generation of projections.

The imaging system further comprises a data processing unit 20 which may particularly comprise a computer (workstation) 21. The computer 21 comprises the usual hardware components like CPU, memory, I/O interfaces and the like together with appropriate software. In FIG. 1, functional components or modules (realized in hardware and software) corresponding to the main processing steps executed by the computer 21 are sketched.

The first module of the computer 21 collects and stores the two-dimensional raw projections 22 generated continuously by the X-ray device 10 during an investigation.

In the next module, the computer 21 reconstructs with methods known in the art (e.g. Backprojection) a three-dimensional representation of a volume of interest 23 from the projections 22. Projection data obtained over an angular range of at least 180° are used for volume reconstruction of said volume. The reconstruction of the volume is continuously updated as soon as new projections covering an angular range of e.g. 30° are available.

In the next step, a virtual projection 24 is calculated or forward projected from the reconstructed volume 23 or a suitable sub-volume thereof. The specific parameters of said virtual projection may be interactively set by a user via a keyboard 27, a mouse 26 and/or a touch screen 25. The calculated virtual projection 24 may then be displayed on a monitor 25 for the assistance of the physician. Optionally two or more virtual projections 24 can be calculated and displayed simultaneously on the monitor 25. Moreover, it is of course also possible to display one or more raw projections 22 or the reconstructed volume 23 on the monitor 25. If a real time display of a volume with higher quality is desired, the dose with which the single raw projections 22 are generated may be increased such that the signal-to-noise-ratio of the projections and thus of the reconstructed volume is improved accordingly (called "high-dose mode"). The user may then switch between two operation modes:

Direct use of the real-time three-dimensional image (RT-3D) information for guidance (high-dose mode);
Indirect use of the RT-3D by calculation of projections from the reconstructed volumes (low-dose mode).

In both modes, the visualization/projection direction can be freely chosen and interactively be modified during the on-going data acquisition.

Further modifications of the invention may include:
an interactive switching between the aforementioned two modes;
an interactive redefinition of the region of interest during the intervention;
a calculation of two projections with slightly different projection directions for stereoscopic display;
a calculation of several projection directions for simultaneous display of the region of interest from multiple projection directions;

a use of the raw projection data to (a) stereo visualization, (b) visualization of several projection directions simultaneously.

The imaging system has the advantage to allow for arbitrary projection directions during intervention guidance, for a three-dimensional intervention guidance, and for the removal of so-called anatomical noise. It may particularly be applied for all X-Ray guided vascular interventions.

FIG. 2 shows three raw projections of a body region with an aneurysm (large images) with superimposed insets representing the calculated virtual projections of a region of interest. The comparison clearly shows the reduction of anatomical noise and the much better delineation of the aneurysm. The projections were generated with a gated reconstruction technique from data obtained on an interventional cardiovascular X-Ray system.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. Imaging system for the generation of X-ray projections of an object in real time, comprising:
    a) a rotational X-ray device for generating low-quality X-ray raw projections of the object from different directions with a low-dose setting over an angular range of at least 180°, and
    b) a data processing unit that is adapted to reconstruct a low-quality volume of interest of the object from a set of said low-quality raw projections and to calculate at least one high-quality virtual projection in an arbitrarily chosen projection direction from (i) the reconstructed low-quality volume of interest or (ii) a part of the reconstructed low-quality volume of interest in real time, wherein the high-quality virtual projection comprises integrated information of low-quality projections from different directions.

2. The imaging system according to claim 1, wherein the rotational X-ray device comprises a cone-beam X-ray source and a two-dimensional X-ray detector.

3. The imaging system according to claim 1, wherein the reconstructed volume is a sub-volume of the volume reconstructed from the set of raw projections.

4. The imaging system according to claim 1, wherein the rotational X-ray device generates a set of low-quality X-ray raw projections sufficient for reconstruction of the low-quality volume of interest with a total dose that corresponds to the dose of a single high-quality X-ray raw projection.

5. The imaging system according to claim 1, wherein the dose of the X-ray device can be interactively switched between different dose levels.

6. The imaging system according to claim 1, wherein the data processing unit updates the reconstructed low-quality volume of interest continuously based on new low-quality X-ray raw projections (i) each time a certain number of new low-quality X-ray raw projections is available, or (ii) each time the X-ray device has moved forward a certain angle.

7. The imaging system according to claim 1, further comprising:
    a display unit for the display displaying one or more of (i) a reconstructed low-quality volume of interest, (ii) low-quality X-ray raw projections, (iii) calculated high-quality virtual projections, and (iv) stereo images thereof.

8. The imaging system according to claim 1, further comprising:
    an input device for the interactive determination of parameters of one or more of (i) the low-quality X-ray raw projections, (ii) the low-quality volume of interest, and (iii) the high-quality virtual projections.

9. A method for the generation of X-ray projections of an object in real time, comprising:
    a) generating low-quality X-ray raw projections of the object from different directions with a low-dose setting over an angular range of at least 180°;
    b) reconstructing a low-quality volume of interest of the object from a set of said low-quality X-ray raw projections; and
    c) calculating at least one high-quality virtual projection in an arbirtrarily chosen projection direction from tithe reconstructed low-quality volume of interest or (ii) a part of the reconstructed low-qualtiy volume of interest in real time, wherein the high-quality virtual projection comprises integrated information of low-quality projections from different directions.

10. A record carrier on which a computer program for the generation of X-ray projections of an object in real time is stored, said program being adapted to execute a method according to claim 9.

* * * * *